United States Patent
Candau

(10) Patent No.: US 7,402,300 B2
(45) Date of Patent: *Jul. 22, 2008

(54) SUNSCREEN COMPOSITIONS COMPRISING LIPOPHILIC UV-SCREENING AGENTS AND HYDROXYALKYLUREA COMPOUNDS

(75) Inventor: Didier Candau, Bievres (FR)

(73) Assignee: L'Oreal, Paris (FR)

( * ) Notice: Subject to any disclaimer, the term of this patent is extended or adjusted under 35 U.S.C. 154(b) by 232 days.

This patent is subject to a terminal disclaimer.

(21) Appl. No.: 11/311,448

(22) Filed: Dec. 20, 2005

(65) Prior Publication Data

US 2006/0177393 A1    Aug. 10, 2006

Related U.S. Application Data

(60) Provisional application No. 60/646,597, filed on Jan. 26, 2005.

(30) Foreign Application Priority Data

Dec. 20, 2004    (FR) .................. 04 53079

(51) Int. Cl.
    A61Q 17/04    (2006.01)
    A61Q 17/00    (2006.01)
    A61Q 19/04    (2006.01)
    A61Q 19/00    (2006.01)
    A61K 8/02     (2006.01)

(52) U.S. Cl. .................. 424/59; 424/60; 424/400; 424/401

(58) Field of Classification Search .................. 424/59, 424/60, 400, 401
See application file for complete search history.

(56) References Cited

U.S. PATENT DOCUMENTS 6,024,944 A    2/2000    Hansenne

2003/0113357 A1    6/2003    Bell et al.

FOREIGN PATENT DOCUMENTS

| DE | 27 03 185 A1 | 8/1978 |
|---|---|---|
| DE | 2703185 A1 | 8/1978 |
| EP | 0 876 812 A2 | 11/1998 |
| EP | 0876812 A2 | 11/1998 |
| EP | 1 535 607 A1 | 6/2005 |
| WO | 98/35649 A1 | 8/1998 |
| WO | WO 98/35649 A1 | 8/1998 |

OTHER PUBLICATIONS

French Search Report corresponding to FR 04/53079, issued on Aug. 5, 2005, 1 page.

*Primary Examiner*—Shelley A. Dodson
(74) *Attorney, Agent, or Firm*—Buchanan, Ingersoll & Rooney, PC

(57) ABSTRACT

Cosmetic, notably anti-sun/sunscreen compositions having increased sun protection effectiveness and improved distribution over keratin materials, e.g., human skin, contain at least one fatty phase and at least one system for screening out UV radiation, and also contain:

(a) at least one lipophilic UV-screening agent, and
(b) at least one hydroxyalkylurea compound of formula (I):

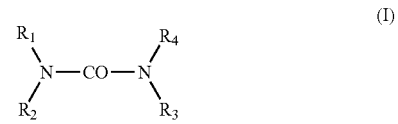

in which $R_1$, $R_2$, $R_3$ and $R_4$ each independently represent a hydrogen atom, a $C_1$-$C_4$ alkyl radical or a $C_2$-$C_6$ hydroxyalkyl radical containing from 1 to 5 hydroxyl groups, at least one of the radicals $R_1$-$R_4$ representing a hydroxyalkyl group, or salt, solvate or isomer thereof, formulated into (c) a topically applicable, cosmetically acceptable carrier therefor.

18 Claims, No Drawings

SUNSCREEN COMPOSITIONS COMPRISING LIPOPHILIC UV-SCREENING AGENTS AND HYDROXYALKYLUREA COMPOUNDS

CROSS-REFERENCE TO PRIORITY/PROVISIONAL APPLICATIONS

This application claims priority under 35 U.S.C. § 119 of FR 04/53079, filed Dec. 20, 2004, and of provisional application Ser. No. 60/646,597, Jan. 26, 2005, each hereby expressly incorporated by reference and each assigned to the assignee hereof.

CROSS-REFERENCE TO COMPANION APPLICATIONS

Copending application Ser. Nos. 11/311,451, 11/311,450, 11/311,650 and 11/311,691, each filed concurrently herewith, each hereby expressly incorporated by reference and each assigned to the assignee hereof.

BACKGROUND OF THE INVENTION

1. Technical Field of the Invention

The present invention relates to sunscreen compositions comprising, formulated into a cosmetically acceptable carrier, at least one fatty phase and at least one system for screening out UV radiation, containing:
 (a) at least one lipophilic UV-screening agent,
 (b) at least one specific hydroxyalkylurea compound.

This invention also relates to the formulation of a hydroxyalkylurea compound of specific formula into a composition comprising, in a cosmetically acceptable carrier, at least one fatty phase and at least one lipophilic UV-screening agent, for increasing the sun protection factor.

2. Description of Background and/or Related and/or Prior Art

It is well known that light radiation with wavelength of from 280 nm to 400 nm permits tanning of the human epidermis and that rays with wavelengths of from 280 to 320 nm, which are known as UV-B rays, cause skin burns and erythema that can harm the development of a natural tan; this UV-B radiation should therefore be screened out.

It is also known that UV-A rays, with wavelengths of from 320 to 400 nm, which cause tanning of the skin, are liable to induce an impairment in the skin, especially in the case of sensitive skin or skin that is continually exposed to solar radiation. UV-A rays in particular bring about a loss of elasticity of the skin and the appearance of wrinkles, leading to premature aging. They promote the triggering of the erythemal reaction or amplify this reaction in certain individuals and may even be the cause of phototoxic or photoallergic reactions. It is therefore desirable also to screen out UV-A radiation.

UV-A and UV-B rays should therefore be screened out, and cosmetic compositions for protecting the human epidermis containing UV-A- and UV-B-screening agents currently exist.

These anti-sun compositions are quite often in the form of an emulsion, of oil-in-water type (i.e., a cosmetically and/or dermatologically acceptable carrier consisting of a continuous aqueous dispersing phase and of a discontinuous fatty dispersed phase), or of water-in-oil type (aqueous phase dispersed in a continuous fatty phase), which contains, in varying concentrations, one or more conventional lipophilic organic screening agents and/or conventional hydrophilic organic screening agents capable of selectively absorbing the harmful UV radiation, these screening agents (and the amounts thereof) being selected as a function of the desired sun protection factor, the sun protection factor (SPF) being expressed mathematically as the ratio of the dose of UV radiation required to reach the erythema-forming threshold with the UV-screening agent to the dose of the UV radiation required to reach the erythema-forming threshold without the UV-screening agent. In such emulsions, the hydrophilic screening agents are present in the aqueous phase and the lipophilic screening agents are present in the fatty phase.

However, this type of anti-sun formulation limits the choice of screening agents, in particular when lipophilic screening agents are involved, since the compositions containing these screening agents have a tendency, after application, to spread out unevenly and to exhibit poor distribution of the screening agents at the surface of the skin, which results in insufficient protection effectiveness.

The inclusion of the lipophilic screening agent octylmethoxycinnamate in a depigmenting lotion containing kojic dipalmitate has already been proposed. This formulation gives no indication for remedying the technical problem mentioned above.

SUMMARY OF THE INVENTION

After considerable research in the field of photoprotection, it has now unexpectedly and surprisingly been determined that, by adding, to a fatty-phase carrier containing at least one lipophilic UV-screening agent, a hydroxyalkylurea of formula (I) more fully described hereinafter, it is possible to obtain anti-sun/sunscreen compositions whose application is substantially improved and which exhibit improved effectiveness. The anti-sun/sunscreen compositions containing such a combination also exhibit good water remanence, perspiration remanence and washing remanence, and also good persistence over time.

In the remainder of the present description, the expression "system for screening out UV radiation" means an agent for screening out UV radiation, comprising either a single organic or inorganic compound for screening out UV radiation, or a mixture of several organic or inorganic compounds for screening out UV radiation, for example a mixture comprising a UV-A-screening agent and a UV-B-screening agent.

In the remainder of the present description, the expression "lipophilic UV-screening agent" means any agent for screening out UV radiation that can be completely dissolved in the molecular state in a fatty phase of the emulsion or else can be solubilized in colloidal form (for example, in micellar form) in a fatty phase.

This discovery forms the basis of the present invention.

Thus, the present invention features compositions comprising, formulated into a cosmetically acceptable carrier, at least one fatty phase and at least one system for screening out UV radiation, and which comprises:
 (a) at least one lipophilic UV-screening agent, and
 (b) at least one hydroxyalkylurea of formula (I) more fully described hereinafter, such compositions containing no kojic dipalmitate.

The present invention also features the use of a hydroxyalkylurea of formula (I), more fully described hereinafter, in a composition comprising, in a cosmetically acceptable carrier, at least one fatty phase and at least one lipophilic UV-screening agent, for increasing sun protection effectiveness.

This invention also features the use of a hydroxyalkylurea of formula (I) more fully described hereinafter, in a composition comprising, in a cosmetically acceptable carrier, at least one fatty phase and at least one lipophilic UV-screening agent, for improving the distribution of said UV-screening agent over the keratin material (such as the skin, eyelashes, eyebrows, nails or mucous membranes).

Other characteristics, aspects and advantages of the invention will become apparent from the detailed description that will follow.

DETAILED DESCRIPTION OF BEST MODE AND SPECIFIC/PREFERRED EMBODIMENTS OF THE INVENTION

The hydroxyalkylureas in accordance with the invention are selected from among those corresponding to general formula (I):

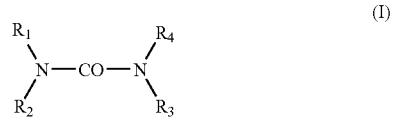

in which $R_1$, $R_2$, $R_3$ and $R_4$ each independently represent a hydrogen atom, a $C_1$-$C_4$ alkyl radical or a $C_2$-$C_6$ hydroxyalkyl radical containing from 1 to 5 hydroxyl groups, at least one of the radicals $R_1$-$R_4$ representing a hydroxyalkyl group, and also the salts, solvates and isomers thereof.

In formula (I), among the alkyl radicals, mention may in particular be made of methyl, ethyl, n-propyl, isopropyl, n-butyl, isobutyl and tert-butyl radicals.

The compounds of formula (I) that are preferred are those that contain only one hydroxyalkyl group, i.e., those for which $R_1$ is a hydroxyalkyl group and $R_2$, $R_3$ and $R_4$ represent, independently of one another, a hydrogen atom or a $C_1$-$C_4$ alkyl radicals. The compounds of formula (I) for which $R_1$ is a hydroxyalkyl group and $R_2$, $R_3$ and $R_4$ each represent a hydrogen atom are more particularly preferred.

Among the hydroxyalkyl groups, preference is given to those containing a single hydroxyl group, and in particular hydroxyethyl, hydroxypropyl, hydroxybutyl, hydroxypentyl and hydroxyhexyl groups. The hydroxyethyl group is preferred.

As compounds of formula (I) that are preferred, mention may be made of N-(2-hydroxyethyl)urea; N-(2-hydroxypropyl)urea; N-(3-hydroxy-propyl)urea; N-(2,3-dihydroxypropyl)urea; N-(2,3,4,5,6-pentahydroxyhexyl)urea; N-methyl-N-(1,3,4,5,6-pentahydroxy-2-hexyl)urea; N-methyl-N'-(1-hydroxy-2-methyl-2-propyl)urea; N-(1-hydroxy-2-methyl-2-propyl)urea; N-(1,3-dihydroxy-2-propyl)urea; N-(trishydroxymethyl-methyl)urea; N-ethyl-N'-(2-hydroxyethyl)urea; N,N-bis-(2-hydroxyethyl)urea; N,N'-bis-(2-hydroxyethyl)urea; N,N-bis-(2-hydroxypropyl)urea; N,N'-bis-(2-hydroxypropyl)urea; N,N-bis-(2-hydroxyethyl)-N'-propylurea; N,N-bis-(2-hydroxypropyl)-N'-(2-hydroxypropyl)urea; N-tert-butyl-N'-(2-hydroxyethyl)-N'-(2-hydroxypropyl)urea; N-(1,3-dihydroxy-2-propyl)-N'-(2-hydroxyethyl)urea; N,N-bis-(2-hydroxyethyl)-N',N'-dimethylurea; N,N,N',N'-tetrakis-(2-hydroxyethyl)urea; and N',N'-bis-(2-hydroxyethyl)-N',N'-bis-(2-hydroxy-propyl)urea.

A compound that is particularly preferred according to the present invention is N-(2-hydroxyethyl)urea, hereinafter referred to as "hydroxyethylurea".

The hydroxyalkylureas of formula (I) can be prepared as described in DE-2703185. Among these, hydroxyethylurea is also commercially available, in the form of a mixture at 50% by weight in water, from the company National Starch under the trademark Hydrovance®.

Among the salts, mention may be made of salts of inorganic acids, such as sulfuric acid, hydrochloric acid, hydrobromic acid, hydriodic acid, phosphoric acid or boric acid. Mention may also be made of the salts of organic acids, which may contain one or more carboxylic, sulfonic or phosphonic acid groups. They may be linear, branched or cyclic aliphatic acids or else aromatic acids. These acids may also contain one or more hetero atoms selected from O and N, for example in the form of hydroxyl groups. Mention may in particular be made of propionic acid, acetic acid, terephthalic acid, citric acid and tartaric acid.

The term "solvate" means a stoichiometric mixture of said compound of formula (I) with one or more molecules of water or of organic solvent, such a mixture being derived from the synthesis of the compound of formula (I).

The hydroxyalkylureas in accordance with the invention are preferably present in the compositions in accordance with the invention at contents of from 0.01 to 50% by weight, and more preferably from 0.1 to 20%, and even more preferably from 0.1 to 10% by weight relative to the total weight of the composition.

Among the lipophilic UV-screening agents that can be used according to the invention, mention may be made of those selected from anthranilates; cinnamic derivatives; dibenzoylmethane derivatives; salicylic derivatives; camphor derivatives; triazine derivatives such as those described in U.S. Pat. No. 4,367,390, EP-863,145, EP-517,104, EP-570,838, EP-796,851, EP-775,698, EP-878,469, EP-933,376, EP-507,691, EP-507,692, EP-790,243, EP-944,624; benzophenone derivatives; β,β-diphenylacrylate derivatives; benzotriazole derivatives; benzalmalonate derivatives, in particular those mentioned in U.S. Pat. No. 5,624,663; benzimidazole derivatives; imidazolines; p-aminobenzoic acid (PABA) derivatives; benzoxazole derivatives as described in EP-0-832,642, EP-1-027,883, EP-1-300,137 and DE-10162844; screening polymers and screening silicones such as those described in particular in WO-93/04665; dimers derived from α-alkylstyrene, such as those described in DE-19855649; 4,4-diarylbutadienes such as those described in DE-19755649, EP-916, 335, EP-1-133,980, EP-1-133,981 and EP-A-1-008,586, and mixtures thereof.

As examples of lipophilic organic screening agents, mention may be made of those denoted above, under their INCI name:

Para-aminobenzoic Acid Derivatives:
Ethyl PABA,
Ethyl dihydroxypropyl PABA,
Ethylhexyl dimethyl PABA marketed in particular under the name "Escalol 507" by ISP.
Salicylic Derivatives:
Homosalate marketed under the name "Eusolex HMS" by Rona/EM Industries,
Ethylhexyl salicylate marketed under the name "Neo Heliopan OS" by
Haarmann and Reimer,
TEA salicylate marketed under the name "Neo Heliopan TS" by Haarmann and Reimer.
Dibenzoylmethane Derivatives:
Butyl methoxydibenzoylmethane marketed in particular under the trademark "Parsol 1789" by Hoffmann Laroche,
Isopropyl dibenzoylmethane.
Cinnamic Derivatives:
Ethylhexyl methoxycinnamate marketed in particular under the trademark "Parsol MCX" by Hoffmann Laroche, Isopropyl methoxycinnamate,
Isoamyl methoxycinnamate marketed under the trademark "Neo Heliopan E 1000" by Haarmann and Reimer,
Cinoxate,
Diisopropyl methylcinnamate.
β,β-Diphenylacrylate Derivatives:
Octocrylene marketed in particular under the trademark "Uvinul N539" by BASF,
Etocrylene marketed in particular under the trademark "Uvinul N35" by BASF.
Benzophenone Derivatives:
Benzophenone-1 marketed under the trademark "Uvinul 400" by BASF,
Benzophenone-2 marketed under the trademark "Uvinul D50" by BASF,
Benzophenone-3 or oxybenzone, marketed under the trademark "Uvinul M40" by BASF,
Benzophenone-6 marketed under the trademark "Helisorb 11" by Norquay,
Benzophenone-8 marketed under the trademark "SpectraSorb UV-24" by American Cyanamid,
Benzophenone-9 marketed under the trademark "Uvinul DS49" by BASF, n-Hexyl 2-(4-diethylamino-2-hydroxybenzoyl)benzoate.
Benzylidenecamphor Derivatives:
3-Benzylidenecamphor manufactured under the name "Mexoryl SD" by Chimex,
4-Methylbenzylidenecamphor marketed under the name "Eusolex 6300" by Merck.
Triazine Derivatives:
Bis-ethylhexyloxyphenol methoxyphenyl triazine marketed under the trademark "Tinosorb S" by Ciba Geigy,
Ethylhexyltriazone marketed in particular under the trademark "Uvinul Ti 50" by BASF,
Diethylhexylbutamidotriazone marketed under the trademark "Uvasorb HEB" by Sigma 3V,
2,4,6-tris(dineopentyl 4'-aminobenzalmalonate)-s-triazine,
2,4,6-tris(diisobutyl 4'-aminobenzalmalonate)-s-triazine.
Benzotriazole Derivatives:
Drometrizole trisiloxane marketed under the name "Silatrizole" by Rhodia Chimie.
Anthranilic Derivatives:
Menthyl anthranilate marketed under the trademark "Neo Heliopan MA" by Haarmann and Reimer.
Imidazoline Derivatives:
Ethylhexyldimethoxybenzylidenedioxoimidazoline propionate.
Benzalmalonate Derivatives:
Dineopentyl 4'-methoxybenzalmalonate,
Polyorganosiloxane containing benzalmalonate functions, such as
Polysilicone-15 marketed under the trademark "Parsol SLX" by Hoffmann Laroche.
4,4-Diarylbutadiene:
1,1-Dicarboxy(2',2'-dimethylpropyl)4,4'-diphenylbutadiene.
Benzoxazole Derivatives:
2,4-bis[5-1(dimethylpropyl)benzoxazol-2-yl(4-phenyl)imino]-6-(2-ethylhexyl)imino-1,3,5-triazine marketed under the name Uvasorb K2A by
Sigma 3V,
and mixtures thereof.

The more particularly preferred lipophilic organic screening agents are selected from among the following compounds:
Homosalate,
Ethylhexyl salicylate,
Ethylhexyl methoxycinnamate,
Octocrylene,
Butyl methoxydibenzoylmethane,
Benzophenone-3,
n-Hexyl 2-(4-diethylamino-2-hydroxybenzoyl)benzoate,
4-Methylbenzylidenecamphor,
2,4,6-tris(dineopentyl 4'-aminobenzalmalonate)-s-triazine,
2,4,6-tris(diisobutyl 4'-aminobenzalmalonate)-s-triazine,
Bis-ethylhexyloxyphenol methoxyphenyl triazine,
Ethylhexyltriazone,
Diethylhexylbutamidotriazone,
Drometrizole trisiloxane,
Polysilicone-15,
Dineopentyl 4'-methoxybenzalmalonate,
1,1-Dicarboxy(2',2'-dimethylpropyl)-4,4-diphenylbutadiene,
2,4-bis[5-1(Dimethylpropyl)benzoxazol-2-yl(4-phenyl)imino]-6-(2-ethylhexyl)imino-1,3,5-triazine,
and mixtures thereof.
Even more preferred are:
Homosalate,
Ethylhexyl salicylate,
Ethylhexyl methoxycinnamate,
Octocrylene,
Butyl methoxydibenzoylmethane,
Ethylhexyltriazone,
Bis-ethylhexyloxyphenol methoxyphenyl triazine,
Diethylhexylbutamidotriazone,
Drometrizole trisiloxane.

The lipophilic screening agents in accordance with the invention are preferably present in the compositions according to the invention at a content ranging from 0.1% to 30% by weight, and preferably from 0.5 to 15% by weight, relative to the total weight of the composition.

The compositions in accordance with the invention may also contain, in addition, one or more organic UV-screening agents that are active in the UV-A range and/or the UV-B range, and that are hydrophilic or else insoluble in the cosmetic solvents commonly used.

Among the hydrophilic organic UV-screening agents that can be used according to the invention, mention may be made of those denoted below under their INCI name:

(1) p-aminobenzoic acid (PABA) derivatives such as:
PABA,
Glyceryl PABA,
PEG-25 PABA marketed under the name "Uvinul P25" by BASF;

(2) benzophenone derivatives comprising at least one sulfonic radical such as:
Benzophenone-4 marketed under the trademark "Uvinul MS40" by BASF,
Benzophenone-5,
Benzophenone-12;

(3) benzylidenecamphor derivatives comprising at least one sulfonic radical, for instance:
Benzylidenecamphorsulfonic acid manufactured under the name "Mexoryl SL" by Chimex,
Camphor benzalkonium methosulfate manufactured under the name "Mexoryl SO" by Chimex,
Terephthalylidenedicamphorsulfonic acid manufactured under the name "Mexoryl SX" by Chimex;

(4) benzimidazole derivatives comprising at least one sulfonic radical, for instance:
Phenylbenzimidazolesulfonic acid marketed in particular under the trademark "Eusolex 232" by Merck,
Benzoazolyl derivatives as described in EP-669,323 and U.S. Pat. No. 2,463,264, and more particularly the compound disodium phenyl dibenzimidazole tetrasulfonate marketed under the trademark "Neo Heliopan AP" by Haarmann and Reimer;

(5) hydrophilic cinnamate derivatives such as, for example, DEA methoxycinnamate; and (6) mixtures thereof.

Among these hydrophilic screening agents, the most preferred are selected from among:

Terephthalylidenedicamphorsulfonic acid,
Benzophenone-4,
Phenylbenzimidazole sulfonic acid,
Disodium phenyl dibenzimidazole tetrasulfonate, and also mixtures thereof.

Among the insoluble organic UV-screening agents, mention may be made of those described in U.S. Pat. Nos. 5,237,071, 5,166,355, GB-2303549, DE-19726184 and EP-893,119, and in particular methylenebis(hydroxyphenyl benzotriazole) derivatives such as methylenebisbenzotriazolyltetramethylbutylphenol marketed in solid form under the trademark "Mixxim BB/100" by Fairmount Chemical or in micronized form in aqueous dispersion under the trademark "Tinosorb M" by Ciba Specialty Chemicals.

The compositions in accordance with the invention may also further comprise one or more supplementary inorganic UV-screening agents.

Among the supplementary inorganic UV-screening agents, mention may be made of pigments (average size of the primary particles: generally from 5 nm to 100 nm, preferably from 10 nm to 50 nm) of metal oxides that are coated or uncoated, such as, for example, pigments of titanium oxide (amorphous or crystallized in rutile and/or anatase form), of iron oxide, of zinc oxide, of zirconium oxide or of cerium oxide, or mixtures thereof. Conventional coating agents are, moreover, alumina and/or aluminum stearate. Such coated or uncoated metal oxide pigments are in particular described in EP-518,772 and EP-518,773.

The supplementary screening agents are preferably present in the compositions according to the invention at a content ranging from 0.1 to 30% by weight, and preferably from 0.5 to 15% by weight, relative to the total weight of the composition.

The compositions according to the invention may be in any of the forms suitable for topical application, in particular in the form of aqueous gels, or in the form of emulsions obtained by dispersion of a fatty phase (also called oily phase) in an aqueous phase (O/W), or vice versa (W/O), or of multiple emulsions (for example, W/O/W or O/W/O or O/O/W). They can be more or less fluid and can have the appearance of a white or colored cream, of an ointment, of a milk, of a lotion, of a serum, of a paste, of a powder or of a solid stick, and can optionally be packaged in an aerosol and be in the form of a foam or of a spray. These compositions are prepared according to the usual methods.

According to a particular embodiment of the invention, the composition according to the invention is in the form of an emulsion and then comprises at least one oily phase. The proportion of the oily phase of the emulsion can range from 1 to 80% by weight, preferably from 2 to 50% by weight, and better still from 2 to 40% by weight, relative to the total weight of the composition. The fatty substances of the oily phase, in particular the oils, and the emulsifiers and coemulsifiers optionally present, used in the composition in the form of an emulsion, are selected from those conventionally used in cosmetics or dermatology. The emulsifier and the coemulsifier, when they are present, are generally so in a proportion ranging from 0.1 to 30% by weight, preferably from 0.3 to 20% by weight, and better still from 0.5 to 15% by weight, relative to the total weight of the composition. The emulsion may also contain lipid vesicles in addition to or instead of the emulsifiers and/or coemulsifiers.

The emulsions generally contain at least one emulsifier selected from among amphoteric, anionic, cationic or nonionic emulsifiers, used alone or as a mixture. The emulsifiers are selected in an appropriate manner according to the continuous phase of the emulsion to be obtained (W/O or O/W). When the emulsion is a multiple emulsion, it generally comprises an emulsifier in the primary emulsion and an emulsifier in the external phase into which the primary emulsion is introduced.

As emulsifiers that can be used for preparing the W/O emulsions, mention may, for example, be made of alkyl esters or ethers of sorbitan, of glycerol or of sugars; silicone surfactants, for instance dimethicone copolyols, such as the mixture of cyclomethicone and of dimethicone copolyol, marketed under the names DC 5225 C and DC 3225 C by Dow Corning, and alkyldimethicone copolyols such as the laurylmethicone copolyol marketed under the name "Dow Corning 5200 Formulation Aid" by Dow Corning, cetyldimethicone copolyol marketed under the name Abil EM 90® by Goldschmidt and the mixture of polyglyceryl-4 isostearate/cetyldimethicone copolyol/hexyl laurate, marketed under the name Abil WE 09® by Goldschmidt. One or more coemulsifiers may also be added thereto, which coemulsifiers may advantageously be selected from the group comprising branched-chain fatty acid esters of polyol, and especially branched-chain fatty acid esters of glycerol and/or of sorbitan, for example polyglyceryl isostearate, such as the product marketed under the name Isolan GI 34 by Goldschmidt, sorbitan isostearate, such as the product marketed under the name Arlacel 987 by ICI, and sorbitan glyceryl isostearate, such as the product marketed under the name Arlacel 986 by ICI, and mixtures thereof.

As emulsifiers that can be used for preparing the O/W emulsions, mention may, for example, be made of nonionic emulsifiers such as oxyalkylenated (more particularly polyoxyethylenated) fatty acid esters of polyols, for example polyethylene glycol stearates, for instance PEG-100 stearate, PEG-50 stearate and PEG-40 stearate; oxyalkylenated fatty acid esters of sorbitan comprising, for example, from 20 to 100 EO, and for example those marketed under the trademarks Tween 20 or Tween 60 by Uniqema; oxyalkylenated (oxyethylenated and/or oxypropylenated) fatty alcohol ethers; alkoxylated or non-alkoxylated sugar esters, for instance sucrose stearate and PEG-20 methylglucose sesquistearate; sorbitan esters such as the sorbitan palmitate marketed under the name Span 40 by Uniqema; esters of diacid and of fatty alcohol, such as dimyristyl tartrate; mixtures of these emulsifiers, for instance the mixture of glyceryl stearate and of PEG-100 stearate (CTFA name: glycerylstearate/PEG-100 stearate) marketed under the name Arlacel 165 by Uniqema and under the name Simulsol 165 by Seppic; or the mixture of dimyristyl tartrate, of cetearyl alcohol, of Pareth-7 and of PEG-25 laureth-25, marketed under the name Cosmacol PSE by Sasol (CTFA name: dimyristyl tartrate/cetearyl alcohol/12-15 Pareth 7/PPG 25 laureth 25).

Coemulsifiers may be added to these emulsifiers, for instance fatty alcohols containing from 8 to 26 carbon atoms, for instance cetyl alcohol, stearyl alcohol and the mixture thereof (cetearyl alcohol), octyldodecanol, 2-butyloctanol, 2-hexyldecanol, 2-undecylpentadecanol or oleyl alcohol, or fatty acids.

Emulsions free of emulsifying surfactants or containing less than 0.5% thereof relative to the total weight of the composition may also be prepared, by using suitable compounds for stabilizing said emulsions, for example amphiphilic polymers, fillers, thickeners or gelling agents.

When the composition of the invention is in emulsion form, it comprises at least one oily phase that contains at least one oil, in particular a cosmetic oil. The term "oil" means a fatty substance that is liquid at room temperature (25° C.).

As oils that can be used in the composition of the invention, use may, for example, be made of hydrocarbon-based oils of animal origin, such as perhydrosqualene (or squalane); hydrocarbon-based oils of plant origin, such as caprylic/capric acid triglycerides, for instance those marketed by Stearineries Dubois or those marketed under the names Miglyol 810, 812 and 818 by Dynamit Nobel, or alternatively oils of plant origin, for example sunflower oil, corn oil, soybean oil, marrow oil, grapeseed oil, sesame oil, hazelnut oil, apricot oil, macadamia oil, arara oil, coriander oil, castor oil, avocado oil, jojoba oil or shea butter oil; synthetic oils; silicone oils, for instance volatile or non-volatile polymethylsiloxanes (PDMS) containing a linear or cyclic silicone chain, which are liquid or pasty at ambient temperature; fluoro oils, such as partially hydrocarbon-based and/or partially silicone-based fluoro oils, for instance those described in document JP-A-2-295912; ethers such as dicaprylyl ether (CTFA name: dicaprylyl ether); and $C_{12}$-$C_{15}$ fatty alcohol benzoates (Finsolv TN from Finetex); arylalkyl benzoate derivatives such as 2-phenylethyl benzoate (X-Tend 226 from ISP); amidated oils such as isopropyl N-lauroylsarcosinate (Eldew SL-205 from Ajimoto), and mixtures thereof.

The oily phase may also comprise one or more fatty substances selected, for example, from fatty alcohols (cetyl alcohol, stearyl alcohol, cetearyl alcohol), fatty acids (stearic acid) or waxes (paraffin, polyethylene wax, carnauba wax, beeswax).

The compositions of the invention may also contain one or more organic solvents which may be selected from the group consisting of hydrophilic organic solvents, lipophilic organic solvents, amphiphilic solvents, or mixtures thereof.

Among the hydrophilic organic solvents, mention may, for example, be made of linear or branched monohydric alcohols containing from 1 to 8 carbon atoms, such as ethanol, propanol, butanol, isopropanol or isobutanol; polyethylene glycols containing from 6 to 80 ethylene oxides; polyols such as propylene glycol, isoprene glycol, butylene glycol, glycerol or sorbitol; monoalkyl or dialkyl isosorbide in which the alkyl groups contain from 1 to 5 carbon atoms, such as dimethyl isosorbide; glycol ethers, such as diethylene glycol monomethyl ether or diethylene glycol monoethyl ether, and propylene glycol ethers such as dipropylene glycol methyl ether.

As amphiphilic organic solvents, mention may be made of polypropylene glycol (PPG) derivatives, such as esters of polypropylene glycol and of a fatty acid, or of PPG and of a fatty alcohol, for instance PPG-23 oleyl ether and PPG-36 oleate.

As lipophilic organic solvents, mention may, for example, be made of fatty esters such as diisopropyl adipate, dioctyl adipate or alkyl benzoates.

The compositions in accordance with the present invention may also comprise conventional cosmetic adjuvants selected from softeners, humectants, opacifiers, stabilizers, emollients, silicones, anti-foams, fragrances, preservatives, anionic, cationic, nonionic, zwitterionic or amphoteric surfactants, fillers, polymers, propellants, basifying or acidifying agents, or any other ingredient normally used in cosmetics and/or dermatology.

As hydrophilic thickeners, mention may be made of carboxyvinyl polymers such as carbopols (carbomers) and Pemulen (acrylate/$C_{10}$-$C_{30}$ alkyl acrylate copolymer); cellulose derivatives such as hydroxyethyl-cellulose; polysaccharides, and in particular gums such as xanthan gum; and mixtures thereof.

As lipophilic thickeners, mention may be made of modified clays such as hectorite and derivatives thereof, for instance the products marketed under the name Bentone.

As preservatives, mention may be made of para-hydroxybenzoic acid esters, also called Parabens® (in particular methyl paraben, ethyl paraben, propyl paraben), phenoxyethanol, compounds which release formaldehyde, such as, for example, imidazolidinylurea or diazolidinylurea, chlorhexidine digluconate, sodium benzoate, caprylyl glycol, iodopropynyl butyl carbamate, pentylene glycol, alkyltrimethylammonium bromide, such as myristyltrimethylammonium bromide (CTFA name: myrtrimonium bromide), dodecyltrimethylammonium bromide, hexadecyltrimethylammonium bromide, and mixtures thereof, such as the mixture marketed under the name Cetrimide® by FEF Chemicals. The preserving agent may be present in the composition according to the invention at a content ranging from 0.001 to 10% by weight, relative to the total weight of the composition, especially ranging from 0.1 to 5% by weight, and in particular ranging from 0.2 to 3% by weight.

As fillers that may be used in the composition of the invention, mention may, for example, be made of pigments; silica powder; talc; polyamide particles, and in particular those marketed under the name Orgasol by Atochem; polyethylene powders; powders of natural organic materials such as starch powders, in particular powders of crosslinked or non-crosslinked cornstarch, wheat starch or rice starch, such as the starch powders crosslinked with octenylsuccinate anhydride marketed under the name Dry-Flo by National Starch; microspheres based on acrylic copolymers, such as those made of ethylene glycol dimethacrylate/lauryl methacrylate copolymer marketed by Dow Corning under the name Polytrap; polymethyl methacrylate powders such as those marketed under the name Micropearl M 100 by Matsumoto; expanded powders such as hollow microspheres, and in particular the microspheres marketed under the name Expancel by Kemanord Plast or under the name Micropearl F 80 ED by Matsumoto; silicone resin microbeads such as those marketed under the name Tospearl by Toshiba Silicone; polyurethane powders such as the hexamethylene diisocyanate/trimethylol hexyl lactone copolymer powder marketed under the name Plastic Powder D-400 by Toshiba Pigment (CTFA name: HDI/trimethylol hexyllactone crosspolymer); and mixtures thereof. When they are present, these fillers may be in amounts ranging from 0.001 to 20% by weight, preferably from 0.1 to 10% by weight, and better still from 1 to 5% by weight, relative to the total weight of the composition.

Of course, one skilled in this art will take care to choose the possible supplementary compound(s) mentioned above and/or the amounts thereof in such a way that the advantageous properties intrinsically associated with the combination in accordance with the invention are not, or are not substantially, impaired by the envisaged addition(s).

The compositions according to the invention are generally suitable for topical application to the skin and therefore generally comprise a physiologically acceptable medium, i.e., a medium compatible with the skin and/or its integuments. It is preferably a cosmetically acceptable medium, i.e., a medium that has a pleasant color, odor and feel and that does not generate any unacceptable discomfort (stinging, tautness, redness) that may dissuade the consumer from using this composition.

The compositions according to the invention may constitute a skincare product, in particular for the face, the neck, the area around the eyes or the body; alternatively a skin makeup product such as a complexion product (especially a foundation), an eyeshadow, a blusher, an eyeliner, a concealer product, a body makeup product, an anti-sun product or else a skin cleansing product. Preferably, the composition according to the invention will be an anti-sun product.

The composition is generally not rinsed off, but it may be rinsed off if it constitutes a cleansing product, in particular a foaming product.

The present invention also features a cosmetic regime or regimen for treating a keratin material such as the skin, the eyelashes, the eyebrows, the nails or the mucous membranes, wherein a composition as defined above is typically applied to the keratin material.

According to another aspect, this invention also features a cosmetic assembly comprising:
 i) a container delimiting at least one compartment, said container being closed by means of a closing member; and
 ii) a composition as described above and placed inside said compartment.

The container may be in any appropriate form. It may in particular be in the form of a bottle, a tube, a jar, a case, a box, a sachet or a carton.

The closing member may be in the form of a removable stopper, a lid, a cap, a tear-off strip or a capsule, in particular of the type comprising a body attached to the container and a cover cap articulated on the body. It may also be in the form of a member for selectively closing the container, in particular a pump, a valve or a flap valve.

The product may be contained directly in the container, or indirectly. By way of example, the product may be arranged on an impregnated carrier, in particular in the form of a wipe or of a pad, and arranged (individually or in plurality) in a box or in a sachet. Such a carrier incorporating the product is described, for example, in WO 01/03538.

The closing member may be coupled to the container by screwing. Alternatively, the coupling between the closing member and the container is done other than by screwing, in particular via a bayonet mechanism, by click-fastening, gripping, welding, bonding or by magnetic attraction. The term "click-fastening" is in particular intended to mean any system involving the crossing of a bead or cord of material by elastic deformation of a portion, in particular of the closing member, followed by return to the elastically unconstrained position of said portion after the crossing of the bead or cord.

The container may be at least partially made of thermoplastic material. By way of examples of thermoplastic materials, mention may be made of polypropylene or polyethylene.

Alternatively, the container is made of non-thermoplastic material, in particular of glass or of metal (or alloy).

The container may have rigid walls or deformable walls, in particular in the form of a tube or of a tubular bottle.

The container may comprise means for distributing or facilitating the distribution of the composition. By way of example, the container may have deformable walls so as to cause the composition to exit in response to a positive pressure inside the container, this positive pressure being caused by elastic (or non-elastic) squeezing of the walls of the container.

The compositions according to the invention may be in the form of sprayable fluid lotions in accordance with the invention that are applied in the form of fine particles by means of pressurization devices. The devices in accordance with the invention are well known to those skilled in the art and comprise non-aerosol pumps or "atomizers", aerosol containers comprising a propellant and also aerosol pumps that use compressed air as propellant. The latter are described in U.S. Pat. Nos. 4,077,441 and 4,850.

The compositions packaged as an aerosol in accordance with the invention generally contain conventional propellants such as, for example, hydrofluoro compounds, dichlorodifluoromethane, difluoroethane, dimethyl ether, isobutane, n-butane, propane or trichlorofluoromethane. They are preferably present in amounts ranging from 15 to 50% by weight relative to the total weight of the composition.

In order to further illustrate the present invention and the advantages thereof, the following specific examples are given, it being understood that same are intended only as illustrative and in nowise limitative. In said examples to follow, all parts and percentages are given by weight, unless otherwise indicated.

| Compositions | Ex 1 | Ex 2 | Ex 3 | Ex 4 | Ex 5 |
|---|---|---|---|---|---|
| PHASE A: | | | | | |
| Polydimethylsiloxane | 0.5 | 0.5 | 0.5 | 0.5 | 0.5 |
| Preservatives | 1.0 | 1.0 | 1.0 | 1.0 | 1.0 |
| Stearic acid | 1.5 | 1.5 | 1.5 | 1.5 | 1.5 |
| Mixture of glyceryl monostearate/PEG (100 EO) stearate | 1.0 | 1.0 | 1.0 | 1.0 | 1.0 |
| Mixture of cetylstearyl glucoside/cetylstearyl alcohol | 2.0 | 2.0 | 2.0 | 2.0 | 2.0 |
| Isohexadecane | 1.0 | 1.0 | 1.0 | 1.0 | 1.0 |
| Cetyl alcohol | 0.5 | 0.5 | 0.5 | 0.5 | 0.5 |
| $C_{12}/C_{15}$ alcoholbenzoate | 5.0 | — | 5 | 5 | — |
| Butyl methoxydibenzoylmethane | 2.0 | 2.5 | 2.0 | 2.0 | 2.0 |
| Octocrylene | 9.0 | 10.0 | 9.0 | — | 10.0 |
| Ethylhexyl triazone | 1.0 | — | 1.0 | — | — |
| Drometrizole trisiloxane | 1.0 | — | 4.0 | — | 5.0 |
| Octylmethylcinnamate | — | 3.0 | — | — | 5.0 |
| Bis-Ethylhexyloxyphenol methoxyphenyl triazine | 1.0 | 3.0 | 1.0 | 3.0 | 3.0 |
| PHASE B: | | | | | |
| N-(2-hydroxyethyl)urea | 5.0 | 10.0 | 5.0 | 5.0 | 10.0 |
| Deionized water | qs 100 | qs 100 | qs 100 | qs 100 | qs 100 |
| Sequestering agent | 0.1 | 0.1 | 0.1 | 0.1 | 0.1 |
| Glycerol | 5.0 | 5.0 | 5.0 | 5.0 | 5.0 |
| Xanthan gum | 0.2 | 0.2 | 0.2 | 0.2 | 0.2 |
| Monocetyl phosphate | 1.0 | 1.0 | 1.0 | 1.0 | 1.0 |
| PHASE C: | | | | | |
| Acrylic acid/stearyl methacrylate copolymer | 0.2 | 0.2 | 0.2 | 0.2 | 0.2 |
| Triethanolamine | qs | qs | qs | qs | qs |

Procedure:

The aqueous phase (phase B) containing all of its ingredients is heated to 80° C. in a water bath. The fatty phase (phase A) containing all of its ingredients is heated to 80° C. in a water bath. A is emulsified in B with stirring of rotor-stator type (device from the company Moritz). Phase C is incorporated and the mixture is allowed to return to ambient temperature with moderate stirring. The triethanolamine is introduced so as to adjust the pH to the desired value at the end of manufacture.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic composition comprising at least one fatty phase and at least one system for screening out UV radiation, and further comprising:

(a) at least one lipophilic UV-screening agent, and
(b) at least one hydroxyalkylurea compound of formula (I):

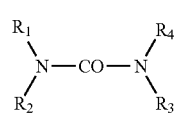

in which $R_1$, $R_2$, $R_3$ and R4 each independently represent a hydrogen atom, a $C_1$-$C_4$ alkyl radical or a $C_2$-$C_6$ hydroxyalkyl radical containing from 1 to 5 hydroxyl groups, at least one of the radicals $R_1$-$R_4$ representing a hydroxyalkyl group, or salt, solvate, or isomer thereof, formulated into (c) a topically applicable, cosmetically acceptable carrier therefore.

2. The cosmetic composition as defined by claim 1, devoid of kojic dipalmitate.

3. The cosmetic composition as defined by claim 1, wherein, in formula (I), $R_1$ is a hydroxyalkyl group and $R_2$, $R_3$ and $R_4$ represent, independently of one another, a hydrogen atom or a $C_1$-$C_4$ alkyl radical.

4. The cosmetic composition as defined by claim 3, wherein, in formula (I), $R_1$ is a hydroxyalkyl group and $R_2$, $R_3$ and $R_4$ each represent a hydrogen atom.

5. The cosmetic composition as defined by claim 1, said at least one compound of formula (I) being selected from the group consisting of N-(2-hydroxyethyl)urea; N-(2-hydroxypropyl)urea; N-(3-hydroxypropyl)urea; N-(2,3-dihydroxypropyl)urea; N-(2,3,4,5,6-pentahydroxyhexyl)urea; N-methyl-N-(1,3,4,5,6-pentahydroxy-2-hexyl)urea; N-methyl-N'-(1-hydroxy-2-methyl-2-propyl)urea; N-(1-hydroxy-2-methyl-2-propyl)urea; N-(1,3-dihydroxy-2-propyl)urea; N-(trishydroxymethylmethyl)urea; N-ethyl-N'-(2-hydroxyethyl)urea; N,N-bis-(2-hydroxyethyl)urea; N,N'-bis-(2-hydroxyethyl)urea; N,N-bis-(2-hydroxypropyl)urea; N,N'-bis-(2-hydroxypropyl)urea; N,N-bis-(2-hydroxyethyl)-N'-propylurea; N,N-bis-(2-hydroxypropyl)-N'-(2-hydroxyethyl)urea; N-tert-butyl-N'-(2-hydroxyethyl)-N'-(2-hydroxypropyl)urea; N-(1,3-dihydroxy-2-propyl)-N'-(2-hydroxyethyl)urea; N,N-bis-(2-hydroxyethyl)-N',N'-dimethylurea; N,N,N',N'-tetrakis-(2-hydroxyethyl)urea; and N',N'-bis-(2-hydroxyethyl)-N',N'-bis-(2-hydroxypropyl)urea; and mixtures thereof.

6. The cosmetic composition as defined by claim 1, wherein said at least one compound of formula (I) is N-(2-hydroxyethyl)urea.

7. The cosmetic composition as defined by claim 1 comprising 0.01 to 50% by weight of said at least one compound of formula (I).

8. The cosmetic composition as defined by claim 1, said at least one lipophilic screening agent being selected from the group consisting of anthranilates; dibenzoylmethane derivatives; cinnamic derivatives; salicylic derivatives; camphor derivatives; benzophenone derivatives; β,β-diphenylacrylate derivatives; triazine derivatives; benzotriazole derivatives; benzalmalonate derivatives; benzimidazole derivatives; imidazolines; bisbenzoazolyl derivatives; p-aminobenzoic acid (PABA) derivatives; benzoxazole derivatives; screening polymers and screening silicones; dimers derived from α-alkylstyrene; and 4,4-diarylbutadienes, and mixtures thereof.

9. The cosmetic composition as defined by claim 8, said at least one lipophilic UV-screening agent being selected from the group consisting of the following compounds:

Homosalate,
Ethylhexyl salicylate,
Ethylhexyl methoxycinnamate,
Octocrylene,
Butyl methoxydibenzoylmethane,
Benzophenone-3,
n-Hexyl 2-(4-diethylamino-2-hydroxybenzoyl)benzoate,
4-Methylbenzylidenecamphor,
2,4,6-tris(dineopentyl 4'-aminobenzalmalonate)-s-triazine,
2,4,6-tris(diisobutyl 4'-aminobenzalmalonate)-s-triazine,
Bis-ethylhexyloxyphenol methoxyphenyl triazine,
Ethylhexyltriazone,
Diethylhexylbutamidotriazone,
Drometrizole trisiloxane,
Polysilicone-15,
Dineopentyl 4'-methoxybenzalmalonate,
1,1-Dicarboxy(2',2'-dimethylpropyl)-4,4-diphenylbutadiene, and 2,4-bis[5-1(Dimethylpropyl)benzoxazol-2-yl(4-phenyl)imino]-6-(2-ethylhexyl)imino-1,3,5-triazine, and
mixtures thereof.

10. The cosmetic composition as defined by claim 9, said at least one lipophilic UV-screening agent being selected from the group consisting of the following compounds:

Homosalate,
Ethylhexyl salicylate,
Ethylhexyl methoxycinnamate,
Octocrylene,
Butyl methoxydibenzoylmethane,
Ethylhexyltriazone,
Bis-Ethylhexyloxyphenol methoxyphenyl triazine,
Diethylhexylbutamidotriazone, and
Drometrizole trisiloxane.

11. The cosmetic composition as defined by claim 1, wherein said at least one lipophilic screening agent comprises from 0.1 to 30% by weight thereof.

12. The cosmetic composition as defined by claim 1, formulated as a skincare product, a skin makeup product, an anti-sun/sunscreen product or a skin cleansing product.

13. The cosmetic composition as defined by claim 1, formulated as an anti-sun/sunscreen product.

14. A regime or regimen for photoprotecting a keratin material against the damaging effects of UV radiation, comprising topically applying thereon a cosmetic composition comprising at least one system for screening out UV radiation, and further comprising:

(a) at least one lipophilic UV-screening agent, and
(b) at least one hydroxyalkylurea compound of formula (I):

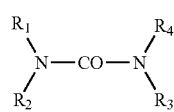

in which $R_1$, $R_2$, $R_3$ and $R_4$ each independently represent a hydrogen atom, a $C_1$-$C_4$ alkyl radical or a C2-C6 hydroxyalkyl radical containing from 1 to 5 hydroxyl groups, at least one of the radicals $R_1$-$R_4$ representing a hydroxyalkyl group, or salt, solvate or isomer thereof, formulated into a topically applicable, cosmetically acceptable carrier therefor.

15. The regime or regimen as defined by claim 14, said keratin material comprising human skin, hair, eyelashes, eyebrows, nails and/or mucous membranes.

16. The regime or regimen as defined in claim 14, for increasing the sun protection effectiveness of said at least one system for screening out UV radiation.

17. The regime or regimen as defined by claim 14, for improving the distribution over the keratin material of said at least one system for screening out UV radiation.

18. A cosmetic assembly comprising:

(i) a container delimiting at least one compartment, said container being closed by means of a closing member; and (ii) a composition as defined by claim 1 and placed inside said compartment.

* * * * *